US010881706B2

(12) United States Patent
Sahin et al.

(10) Patent No.: US 10,881,706 B2
(45) Date of Patent: Jan. 5, 2021

(54) PRODUCT CONTAINING PLANT DERIVED EXOSOMES

(71) Applicant: YEDITEPE UNIVERSITESI, Istanbul (TR)

(72) Inventors: Fikrettin Sahin, Istanbul (TR); Merve Yildirim, Istanbul (TR); Polen Kocak, Istanbul (TR); Burge Ulukan, Istanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 0 days.

(21) Appl. No.: 16/482,719

(22) PCT Filed: Jan. 31, 2018

(86) PCT No.: PCT/TR2018/050034
§ 371 (c)(1),
(2) Date: Aug. 1, 2019

(87) PCT Pub. No.: WO2019/027387
PCT Pub. Date: Feb. 7, 2019

(65) Prior Publication Data
US 2020/0230196 A1 Jul. 23, 2020

(30) Foreign Application Priority Data

Feb. 1, 2017 (TR) .................. 2017 01544

(51) Int. Cl.
*A61K 36/899* (2006.01)
*A61K 36/9068* (2006.01)
*A61K 36/8962* (2006.01)

(52) U.S. Cl.
CPC ........ *A61K 36/899* (2013.01); *A61K 36/8962* (2013.01); *A61K 36/9068* (2013.01)

(58) Field of Classification Search
None
See application file for complete search history.

(56) References Cited

U.S. PATENT DOCUMENTS

2016/0045448 A1* 2/2016 Zhang .................. A61K 9/5176
514/249
2016/0346334 A1 12/2016 Trujillo

FOREIGN PATENT DOCUMENTS

| DE | 202015106158 U1 | 2/2016 |
| WO | 2009051470 A1 | 4/2009 |
| WO | 2016166716 A1 | 10/2016 |
| WO | WO 2016/166716 | * 10/2016 |

OTHER PUBLICATIONS

Mu, J. et al. Interspecies Communication Between Plant and Mouse Gut Host Cells Through Edible Plant Derived Exosome Like Nanoparticles. Molecular Nutrition & Food Research 58(7)1561-1573, Jul. 2014. (Year: 2014).*
Record, M. Exosome Like Nanoparticles from Food. Molecular Therapy 21(7)1294-1296, Jul. 2013. (Year: 2013).*
Canup, B. et al. Targeting Liver Inflammation Caused by Palmitic Acid . . . Gastroenterology 150(4, Suppl 1) S1091, May 2016. (Year: 2016).*
Johnstone Rose M., et al. Vesicle Formation During Reticulocyte Maturation. Association of Plasma Membrane Activities with Released Vesicles (Exosomes). The Journal of Biological Chemistry. Jul. 5, 1987, vol. 262, No. 19, pp. 9412-9460.
Valadi Hadi, et al. Exosome-Mediated Transfer of mRNAs and MicroRNAs is a Novel Mechanism of Genetic Exchange between Cells. Nature Cell Biology. Jun. 2007, vol. 9, No. 6, pp. 654-659.
Thery Clotilde, et al. (2009). Membrane Vesicles as Conveyors of Immune Responses. Nature Reviews, Aug. 2009 vol. 9: 581-593.
Gogolak Peter, et al. Targeting Dendritic Cells for Priming Cellular Immune Responses. Journal of Molecular Recognition, 2003, 16:299-317.
Rani Sweta, et al. The Exosom-A Naturally Secreted Nanoparticle and its Application to Wound Healing. Advanced Materials, Dec. 17, 2015, 28(27), 5542-5552.
Escola, Jean-Michel, et al. Selective Enrichment of Tetraspan Proteins on the Internal Vesicles of Multivesicular Endosomes and on Exosomes Secreted by Human B-lymphocytes. The Journal of Biological Chemistry, Aug. 7, 1998, vol. 273 No. 32, pp. 20121-20127.
Buschow, Sonja I, et al. MHC Class II-Associated Proteins in B-cell Exosomes and Potential Functional Implications for Exosome Biogenesis. Immunology and Cell Biology. May 11, 2010, 88:851-856.
Simpson Richard J. et al. Exosomes: Proteomic Insights and Diagnostic Potential. Expert Reviews Proteomics. 2009, vol. 6 No. 3 pp. 267-283.
Mehmet E. Yalvac. Comparison and Optimisation of Transfection of Human Dental Folliclecells, a Novel Source of Stem Cells, with Different Chemical Methods and Electro-Poration. Neuro chemical research, 2009, 34(7), 1272-1277.
Vermeulen P. B. et al. Microvessel Density, Endothelial Cell Proliferation and Tumour Cell Proliferation in Human Colorectal Adenocarcinomas. Annals of Oncology, 1995, 6(1), 59-64.

* cited by examiner

*Primary Examiner* — Ralph J Gitomer
(74) *Attorney, Agent, or Firm* — Bayramoglu Law Offices LLC

(57) ABSTRACT

A product containing plant derived exosome that may be used in cancer treatment and wound healing. The product enables to provide a low-cost product, which does not cause toxic effects in human body, does not cause damage in the healthy cells during the course of the cancer treatment, does not pose any infection risk since it does not require any procedure such as radiotherapy or surgery, and the side effects occurring in chemotherapy treatment are not experienced. Wheatgrass, garlic and ginger can be used alone or in combination in the product as the plant source.

7 Claims, 8 Drawing Sheets

PRODUCT CONTAINING PLANT DERIVED EXOSOMES

CROSS REFERENCE TO THE RELATED APPLICATIONS

This application is the national phase entry of International Application No. PCT/TR2018/050034, filed on Jan. 31, 2018, which is based upon and claims priority to Turkish Patent Application No. 2017/01544, filed on Feb. 1, 2017, the entire contents of which are incorporated herein by reference.

TECHNICAL FIELD

The present invention relates to a product containing plant derived exosome that may be used in cancer treatment and wound healing.

BACKGROUND

In multi-cell organisms, communication realized as a result of binding of the proteins released from a cell to the receptors on the surface of another cell is the fundamental principle of intercellular communication. Although not much information is known about them, exosomes are the leading communication molecules which are substantially demanded nowadays. Although they were named as the material undesired by the cell and as cell waste when first discovered, it was proved as a result of the researches conducted that exosomes play a substantial role in the immune system. Exosomes are vesicles with sizes of 20-130 nm (nanosized) which are produced by all cells within the plasma and released out of the cell. As discovered recently, these vesicles play a role in endocrine system to provide autocrine and paracrine signals to the local or distal host cells. These exosomes are also responsible for carrying proteins, fats, nucleic acid materials (all RNA types) and transferring them to the recipient cells. This way, the messages that are to be conveyed out of the cells are conveyed to the other neighboring cells. Tetraspanin family is a protein group which is most frequently encountered on the exosome surface. This family includes CD9, BCD63, CD81, CD82, CD83 proteins. The tetraspanin family proteins have the ability to interact with MHC and integrin proteins. No matter how much it is tried to be generalized, the exosome protein pool is rather cell-specific, so it is dependent on the cell from which it is released. Therefore, various (heat-shock) proteins are members of this pool (hsp70). At the same time, the proteins found in the cytoskeleton namely β-actin, tubulin, myosin, cofilin, basic histocompatibility component class I-II molecules and glycer aldehyde 3 phosphate dehydrogenase are the major common proteins of the exosome protein pool. In order for the exosome to be received into the cells to which it will be conveyed, it should stimulate the cell surface receptors of the other cell. Therefore, Wnt-β-catenin signal proteins, notchligang, delta-like 4 proteins and interleukins should be on the exosome surface. Otherwise, it will not be possible for the exosome to stimulate the host cell to which it will convey a message.

In a study, the fact that exosomes obtained from mammalian cells have the potential to be used in cancer treatment is proved (Reghu et al. 2016). In addition to this, it was shown that exosomes have anticarcinogenic activity on mammalian cancer cells (Ohno et al. 2013). In another study conducted similarly, it was determined that exosomes obtained from brain epithelium demonstrated activity against brain cancer (Reriro et al. 2015).

Wheat (*Triticum Aestivum*) plays an important role in human diet within the plant-based diet classification. In accordance with the epidemiological studies conducted, it was proved to play a protective role in chronic thalassemia and cancer patients. Many forms of wheat (wheatgrass or seed (germ)) have been developed for use in cancer treatment. Likewise, ginger and garlic are also antioxidant. In the studies conducted, animal derived exosomes have been used for different applications. In addition, although it is determined that plant derived exosomes are antioxidant, it is observed that there is a huge lack of study about them. As far as is known, plant exosomes show similar properties with mammalian exosomes.

Treatment methods such as surgical operations, radiotherapy and chemotherapy, which target dividing cells, many times result with relapse of cancer or occurrence of a large number of side effects (Kubota, 2012).

The United States patent document no. US2016346334 discloses about exosome cells isolated from healthy cells for use in treatment of breast cancer.

Thanks to the present invention, an alternative method of treatment has been developed so as to cause the death of cancerous cells without harming the healthy cells by means of the product containing the plant exosome. Besides, the fact that exosomes are cellfree products has enabled to prevent problems that might be caused by cellular therapy. Exosomes are ready-to-use therapeutic agents. They can be stored at low temperatures without requiring use of toxic cryopreservative agents and ultra-freezers, and can be safely delivered to the patients. Based on this information, it is aimed to use wheatgrass, garlic and ginger, which are used in alternative medicine, in cancer treatment and as wound healers.

SUMMARY

The object of the present invention is to provide a product containing plant derived exosome which can be used in cancer treatment.

Another object of the present invention is to provide a product which does not cause toxic effects in human body.

A further object of the present invention is to provide a product which is effective in wound healing and injured tissue repair.

Another object of the present invention is to provide a product, during use of which the side effects occurring in chemotherapy treatment are not experienced.

Another object of the present invention is to provide a product which does not cause damage in the healthy cells during the course of cancer treatment.

A further object of the present invention is to provide a product which does not pose any infection risk since it does not require any procedure such as radiotherapy or surgery.

Another object of the present invention is to provide a low-cost product.

A further object of the present invention is to provide a natural product by which chemical contamination arising in the body due to synthetic drugs is not experienced.

Another object of the present invention is to provide a practical and easy-to-access product since the plants to be used in the treatment easily grow and a substantial amount of exosomes is obtained in a short period of time.

BRIEF DESCRIPTION OF THE DRAWINGS

"A Product Containing Plant Derived Exosomes" developed to fulfill the objects of the present invention is illustrated in the accompanying figures wherein.

DETAILED DESCRIPTION OF THE EMBODIMENTS

In accordance with these results, it is shown that the plant exosome only leads cancer cells to apoptosis causing death of the said cells, but does not cause any cell death in the healthy cells.

Experimental Study

Preparation of Plant Derived Exosome

In the inventive product containing plant derived exosome; wheat grass, ginger and garlic can be used alone or in combination as the source of plant. The wheatgrass preferably selected in the experimental studies was obtained from Turkey, Adana Ceyhan 69 seeds. During the work for preliminary sample preparation, it was determined that it was adequate for the seeds to grow for a period of 1.5 weeks.

The collected wheatgrass was first ground in 1% PBS (phosphate buffered saline) and then filtered. The obtained filtrate wheatgrass was centrifuged at 1000×g for 10 minutes, 3200×g for 20 minutes, 15000×g for 60 minutes, and then the cell culture was isolated by using exosome isolation kit. The isolated exosomes were dissolved in 0.9% isotonic serum.

Figure 1A:
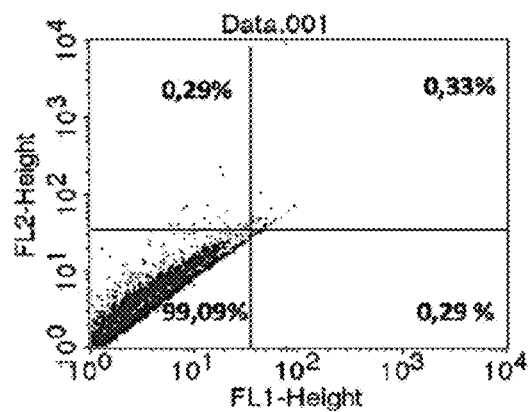
FIG. 1A is a view of the flow cytometry values of the control group of A498 kidney cancer cells.
Figure 1B:
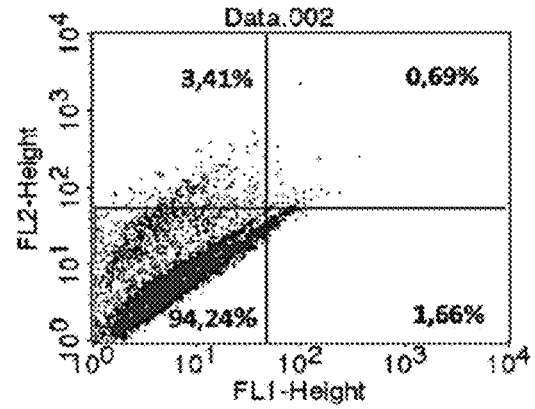
FIG. 1B is a view of the flow cytometry values of the control group of A498 kidney cancer cells with Annexin V staining.
Figure 1C:
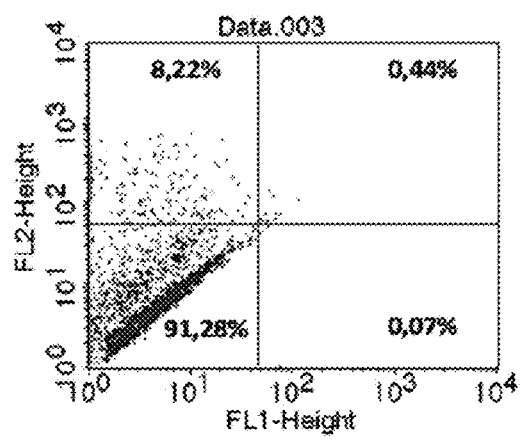
FIG. 1C is a view of the flow cytometry values of the control group of A498 kidney cancer cells with PI staining.
Figure 1D:
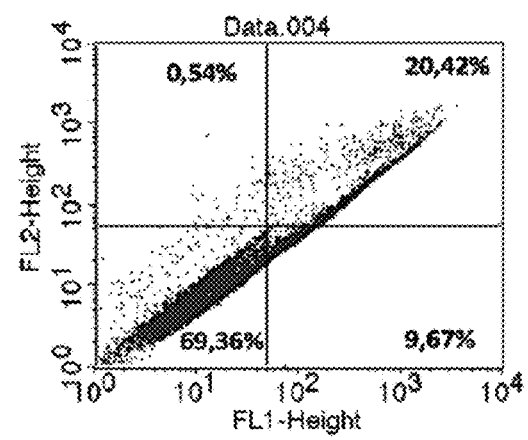
FIG. 1D is a view of the flow cytometry death values of the A498 kidney cancer cells to which 15 mg/ml wheat exosome was applied.
Figure 1E:
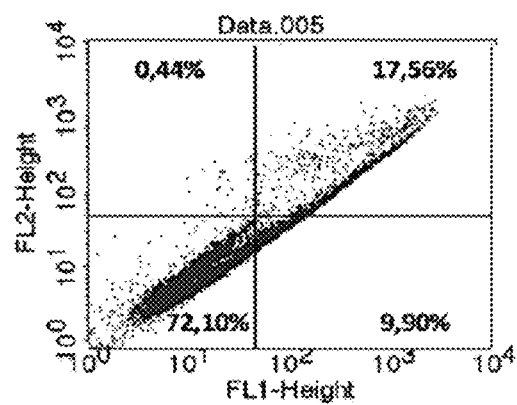
FIG. 1E is a view of the flow cytometry death values of the A498 kidney cancer cells to which 15 mg/ml ginger exosome was applied.
Figure 1F:
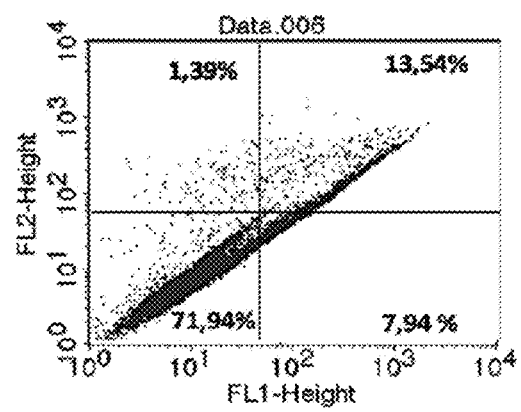
FIG. 1F is a view of the flow cytometry death values of the A498 kidney cancer cells to which 15 mg/ml garlic exosome was applied.
Figure 2A:
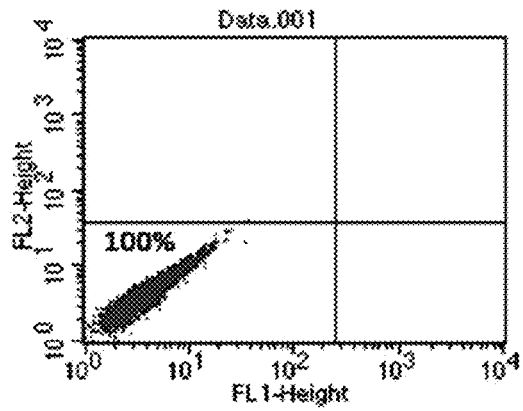
FIG. 2A is a view of the flow cytometry values of the control group of HEK 293 kidney epithelial cells.
Figure 2B:
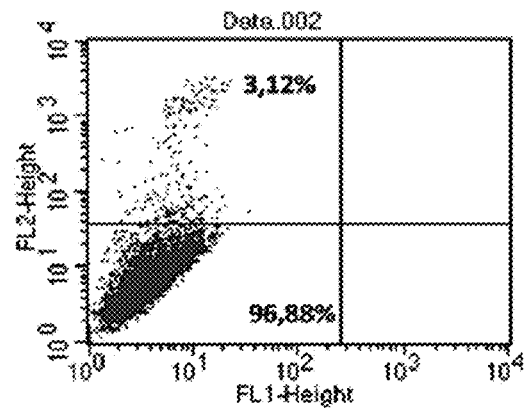
FIG. 2B is a view of the flow cytometry values of the control group of HEK 293 kidney epithelial cells with PI staining.
Figure 2C:
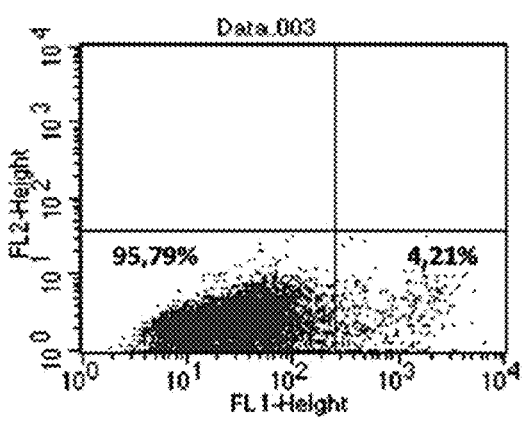
FIG. 2C is a view of the flow cytometry values of the control group of HEK 293 kidney epithelial cells with Annexin V staining.
Figure 2D:
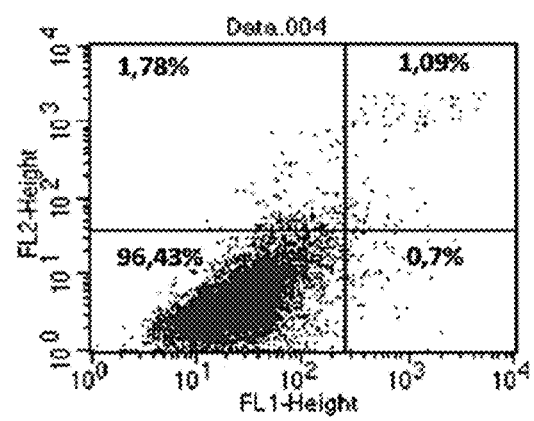
FIG. 2D is a view of the flow cytometry death values of the HEK 293 kidney epithelial cells to which 15 mg/ml wheat exosome was applied.
Figure 2E:
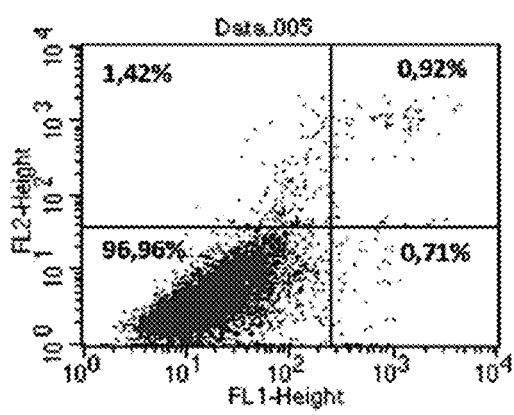
FIG. 2E is a view of the flow cytometry death values of the HEK 293 kidney epithelial cells to which 15 mg/ml ginger exosome was applied.
Figure 2F:
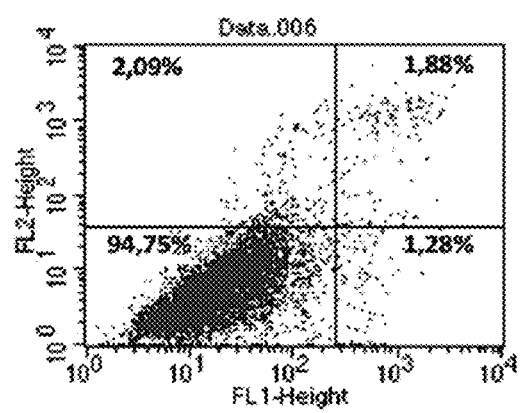
FIG. 2F is a view of the flow cytometry death values of the HEK 293 kidney epithelial cells to which 15 mg/ml garlic exosome was applied.
Figure 3A:
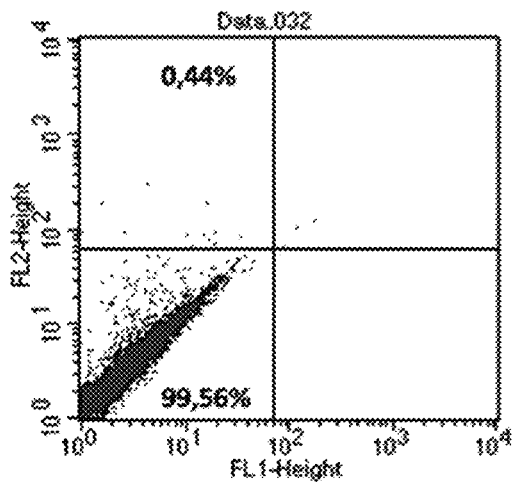
FIG. 3A is a view of the flow cytometry values of the control group of 22RV1 prostate cancer cells.
Figure 3B:
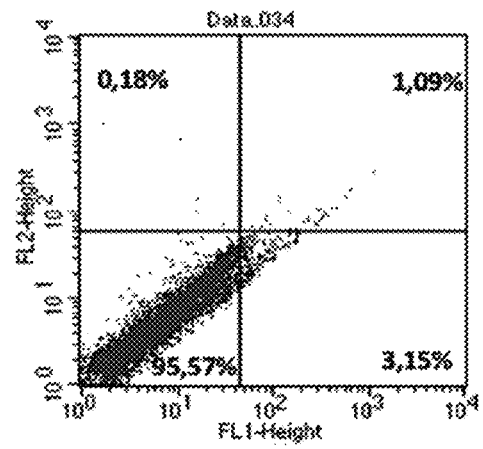
FIG. 3B is a view of the flow cytometry values of the control group of 22RV1 prostate cancer cells with Annexin V staining.
Figure 3C:
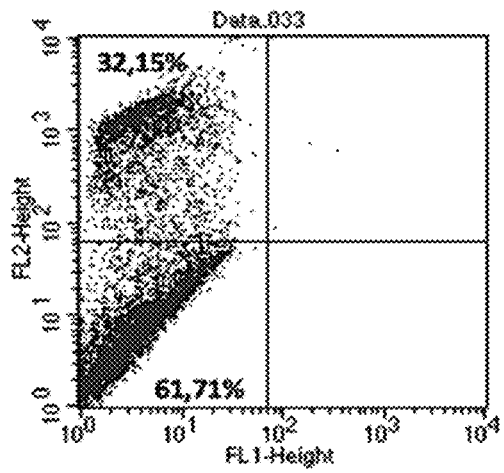
FIG. 3C is a view of the flow cytometry values of the control group of 22RV1 prostate cancer cells with PI staining.
Figure 3D:
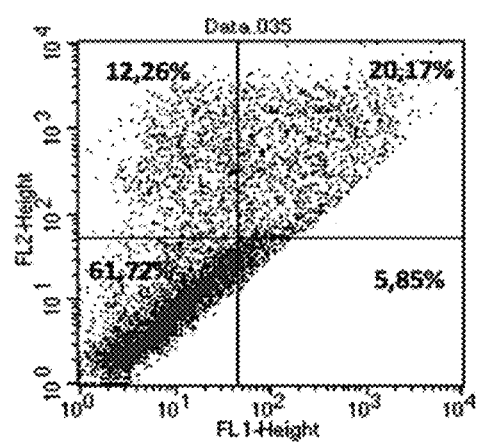
FIG. 3D is a view of the flow cytometry death values of the 22RV1 prostate cancer cells to which 15 mg/ml wheat exosome was applied.
Figure 3E:
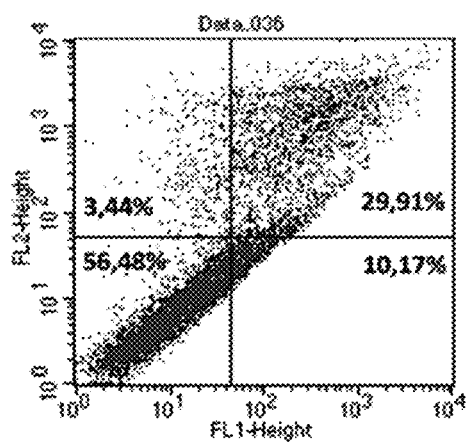
FIG. 3E is a view of the flow cytometry death values of the 22RV1 prostate cancer cells to which 15 mg/ml ginger exosome was applied.
Figure 3F:
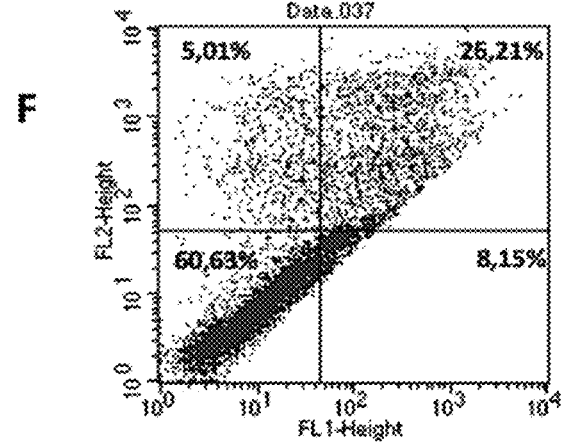
FIG. 3F is a view of the flow cytometry death values of the 22RV1 prostate cancer cells to which 15 mg/ml garlic exosome was applied.
Figure 4A:
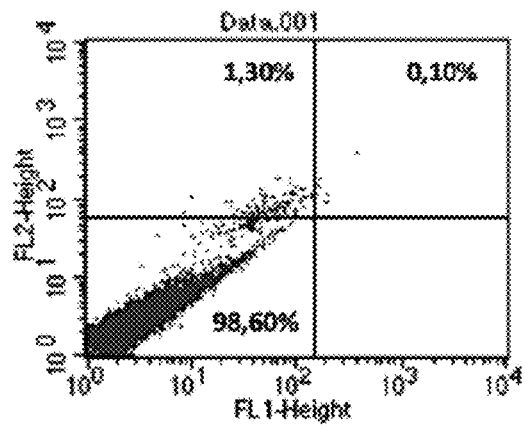
FIG. 4A is a view of the flow cytometry values of the control group of PNT1A prostate epithelial cells.
Figure 4B:
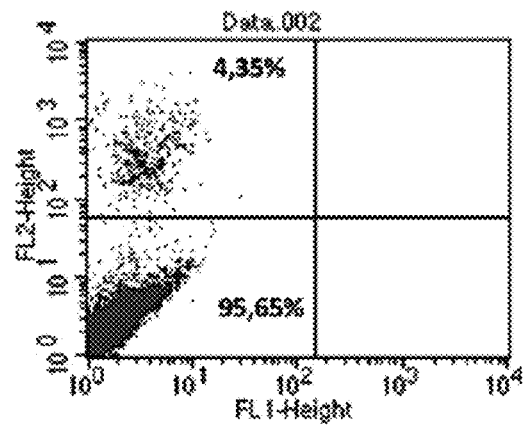
FIG. 4B is a view of the flow cytometry values of the control group of PNT1A prostate epithelial cells with PI staining.
Figure 4C:
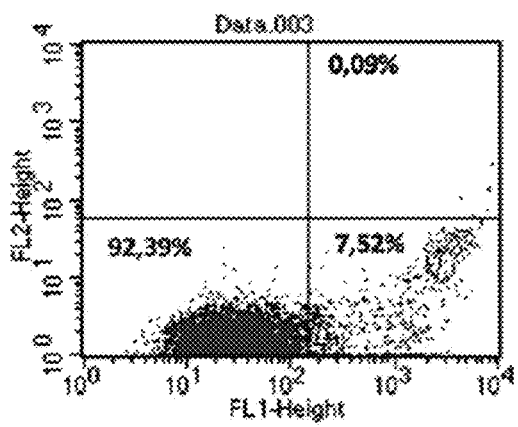
FIG. 4C is a view of the flow cytometry values of the control group of PNT1A prostate epithelial cells with Annexin V staining.
Figure 4D:
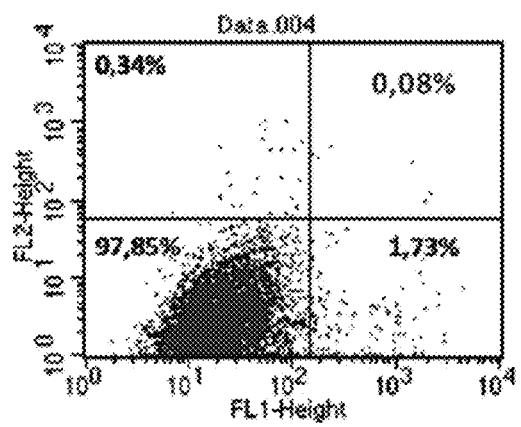
FIG. 4D is a view of the flow cytometry death values of the PNT1A prostate epithelial cells to which 15 mg/ml wheat exosome was applied.
Figure 4E:
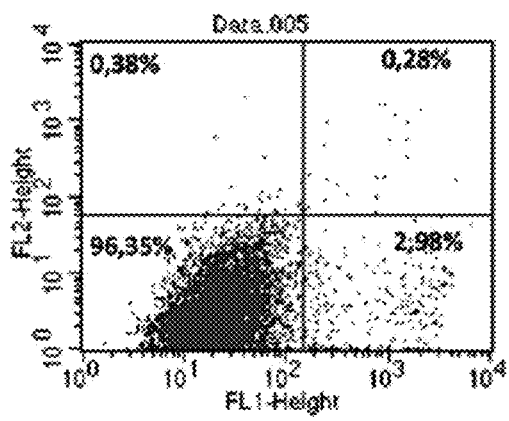
FIG. 4E is a view of the flow cytometry death values of the PNT1A prostate epithelial cells to which 15 mg/ml ginger exosome was applied.
Figure 4F:
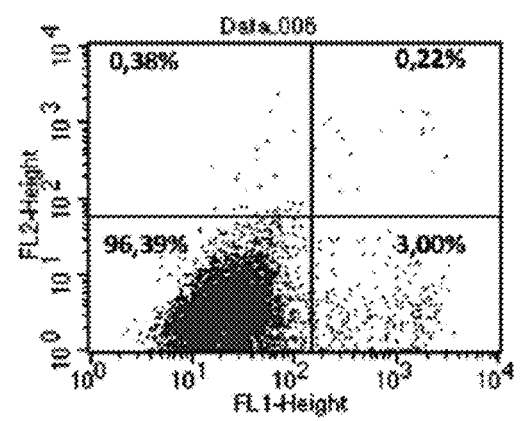
FIG. 4F is a view of the flow cytometry death values of the PNT1A prostate epithelial cells to which 15 mg/ml garlic exosome was applied.
Figure 5A:
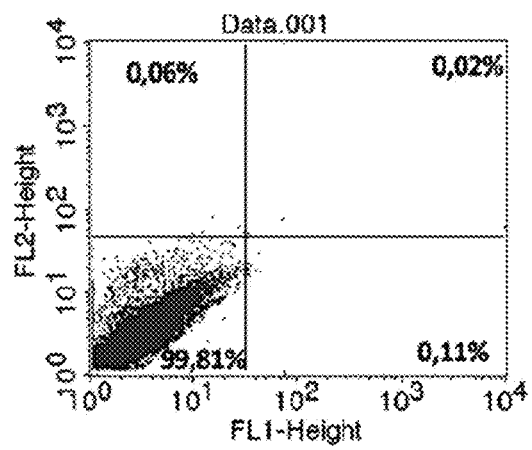
FIG. 5A is a view of the flow cytometry values of the control group of MCF 7 breast cancer cells.
Figure 5B:
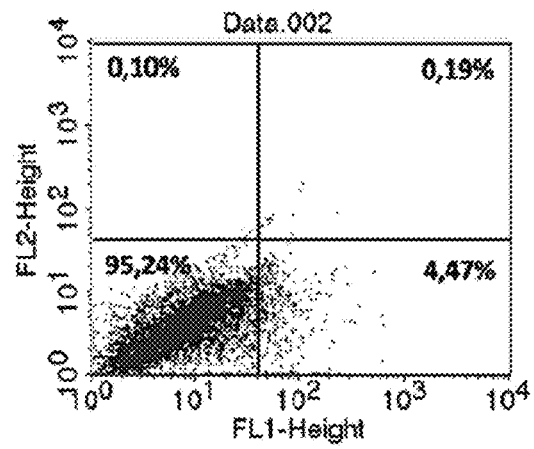
FIG. 5B is a view of the flow cytometry values of the control group of MCF 7 breast cancer cells with Annexin V staining.
Figure 5C:
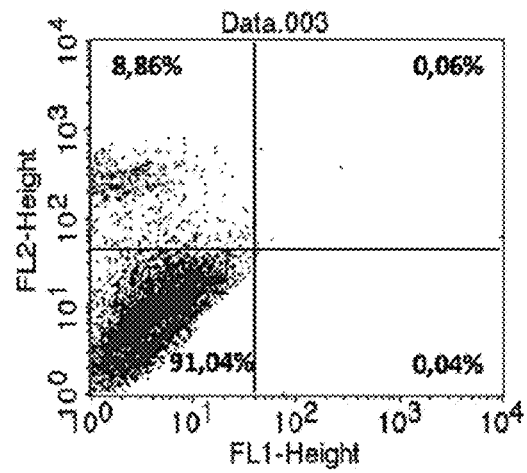
FIG. 5C is a view of the flow cytometry values of the control group of MCF 7 breast cancer cells with PI staining.
Figure 5D:
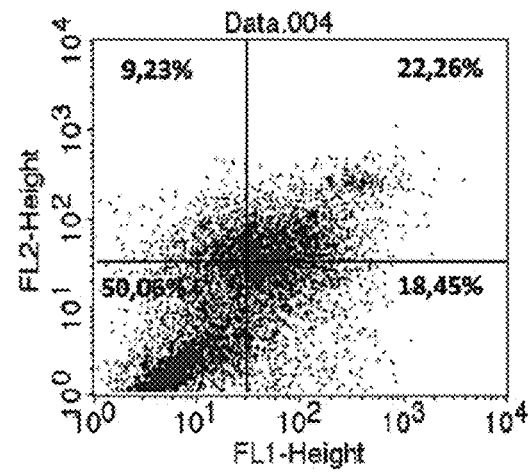
FIG. 5D is a view of the flow cytometry death values of the MCF 7 breast cancer cells to which 15 mg/ml wheat exosome was applied.
Figure 5E:
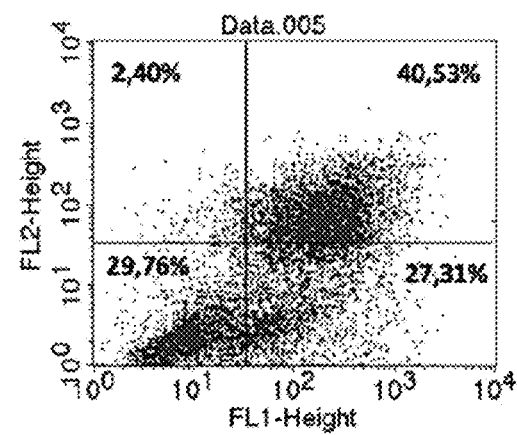
FIG. 5E is a view of the flow cytometry death values of the MCF 7 breast cancer cells to which 15 mg/ml ginger exosome was applied.
Figure 5F:
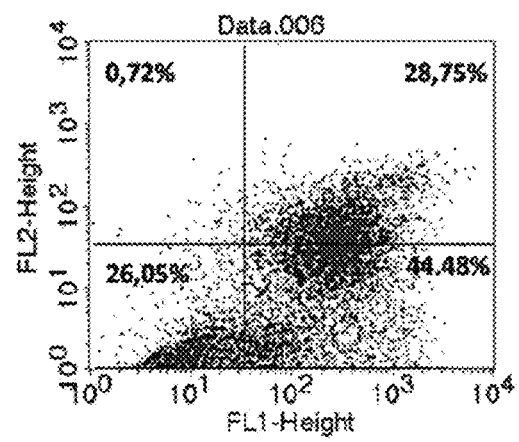
FIG. 5F is a view of the flow cytometry death values of the MCF 7 breast cancer cells to which 15 mg/ml garlic exosome was applied.
Figure 6A:
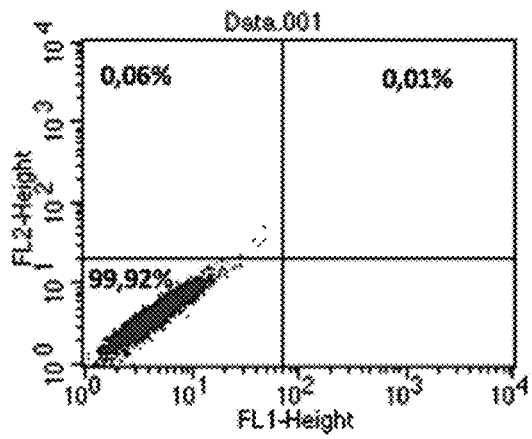
FIG. 6A is a view of the flow cytometry values of the control group of MCF 10A breast epithelial cells.
Figure 6B:
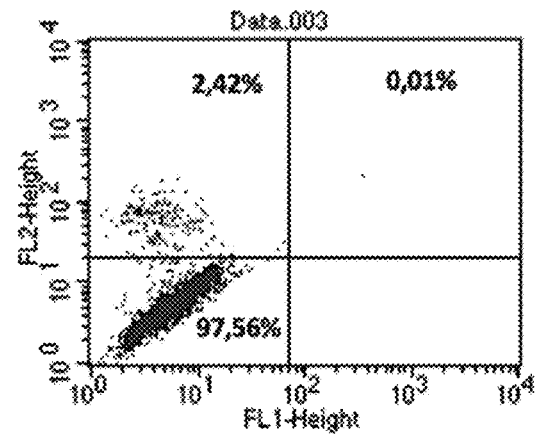
FIG. 6B is a view of the flow cytometry values of the control group of MCF 10A breast epithelial cells with PI staining.
Figure 6C:
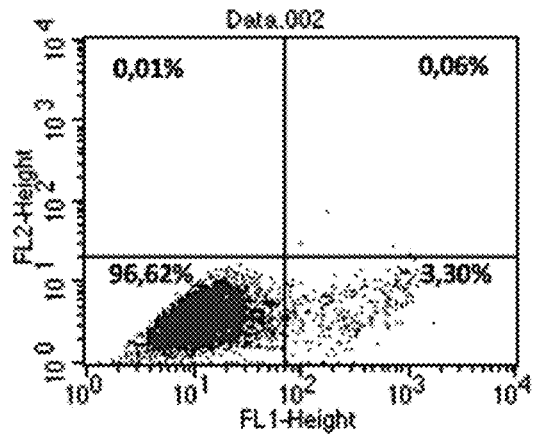
FIG. 6C is a view of the flow cytometry values of the control group of MCF 10A breast epithelial cells with Annexin V staining.
Figure 6D:
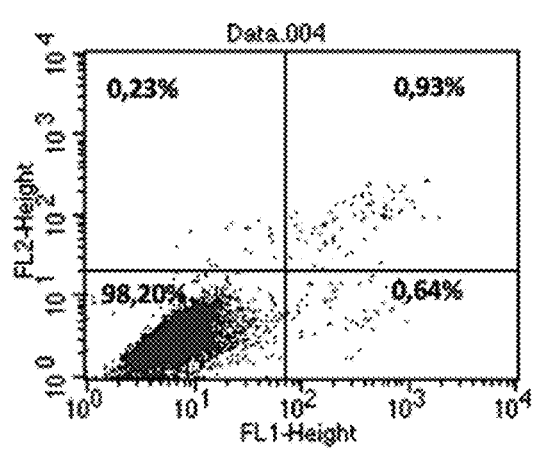
FIG. 6D is a view of the flow cytometry death values of the MCF 10A breast epithelial cells to which 15 mg/ml wheat exosome was applied.
Figure 6E:
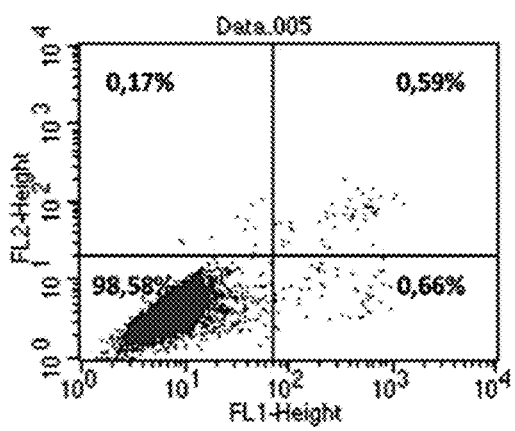
FIG. 6E is a view of the flow cytometry death values of the MCF 10A breast epithelial cells to which 15 mg/ml ginger exosome was applied.
Figure 6F:
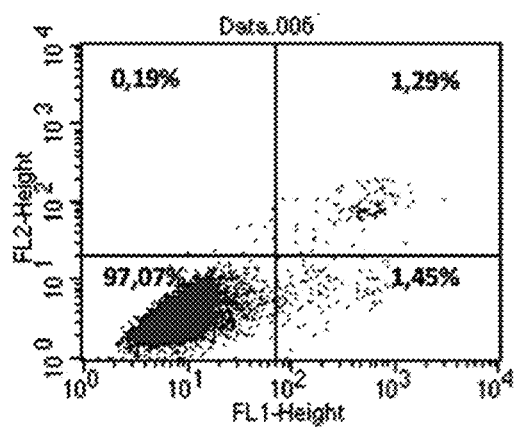
FIG. 6F is a view of the flow cytometry death values of the MCF 10A breast epithelial cells to which 15 mg/ml garlic exosome was applied.
Figure 7:
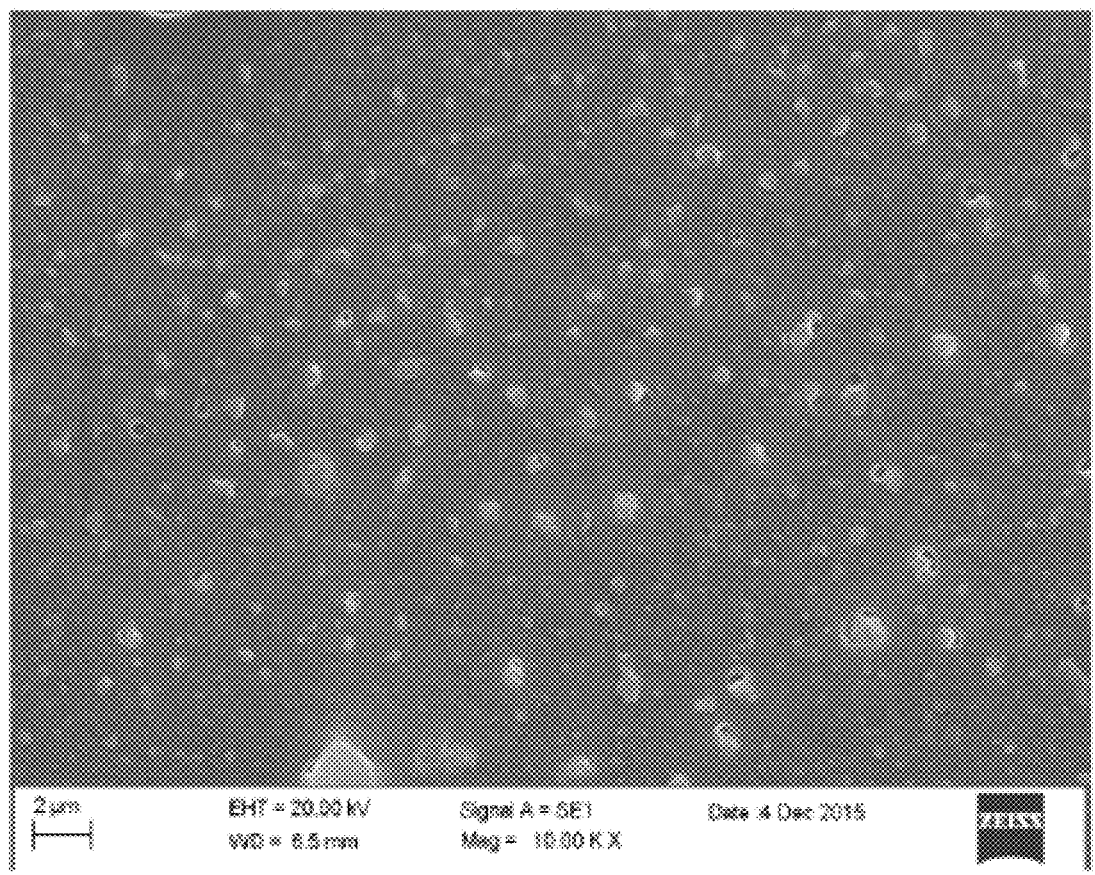
FIG. 7 is the Electron Microscope image wherein presence of the plant exosome obtained from wheat plant is determined.

The inventive product exosomes, which were isolated and were in the serum form, were observed by using scanning electron microscope (FIG. 7). Then, they were incubated by HSP 70 marker and presence of exosomes in the flow cytometry was observed.

Developing the Treatment

Determining Cell Toxicity

Toxic effect of the prepared inventive product was determined by using the MTS method given in the literature (Yalvac et al., 2009).

The chemical molecules were prepared in the medium at specified concentrations and applied on the HEK (human kidney epithelial cell), MCF 10A (human mammalian epithelial cell) and PNT1A (human prostate epithelial cell) cell lines which were seeded on 96-well culture plates (5000 cells/well) by counting. The response of the cells to toxicity of the chemicals was determined by measuring cell viability for 4 days. Cell viability analysis was performed according to MTS method. MTS is a colorimetric method used for measuring mitochondrial enzyme activity. Different doses were applied to the cells which were seeded in the wells in advance, and the effect of the applied substance on viability within the determined period of time was examined. The MTS agent applied upon being mixed with the media acquires a dark color upon increase of the number of viable cells. The resulting color change was evaluated based on the absorbance measurement by using ELISA plate reader. The product developed in the scope of the present invention is prepared so as to attain results at 5 ng/ml, 10 ng/ml, 15 ng/ml concentrations at hours 24, 48, 72 and 96 in healthy cells.

Cancer Cell Death Analysis

In order to examine the effect of the inventive product on cancer, the presence of Annexin V protein, one of the most significant proteins of the pathway of apoptosis, which is a suicide mechanism, has been examined. PI (Propidium Iodide) stain was used to determine the presence of necrosis.

22RV1 (prostate cancer cell), MCF 7 (breast cancer cell), A498 (kidney cancer cell) cells were seeded in 6 well culture plates at 300,000 cells/well. 10% FBS (Fetal Bovine Serum) and 1% PSA (Penicillin Streptomycin Amphotericin) were added to high glucose media o RPMI for 22RVI cell line and DMEM for and MCF 7 and A498 cell lines, thereby enabling the cells to grow. Death rates of the cells which were treated at the specified concentrations were examined after 24 hours. The results have shown that the cell bound to Annexin V antibody underwent or were about to undergo apoptosis and that the cell bound to PI antibody was led to or was about to be led to necrosis. In view of the presence of these antibodies, it was determined that the applied treatment killed the cell.

The same experiment protocol was also applied to MCF10-A, PNT1-A and HEK cell lines which are healthy cell lines.

Examination of the Wound Healing

In addition to use of the product of the present invention in cancer treatment, use thereof in wound healing was also examined. In the experimental study conducted to this end, the healthy cell line HEK cells were seeded in 6 well culture plates. A wound model was formed by making a scratch that goes through the center of the wells. Product containing exosome was applied to the cells on which a wound model was formed. The cells were incubated for 48 hours in the product with a 15 ng/ml concentration and DMEM medium containing 2% FBS. The wound healing process was observed step by step by taking photographs every day under the microscope.

Experimental Results

Figure 8:
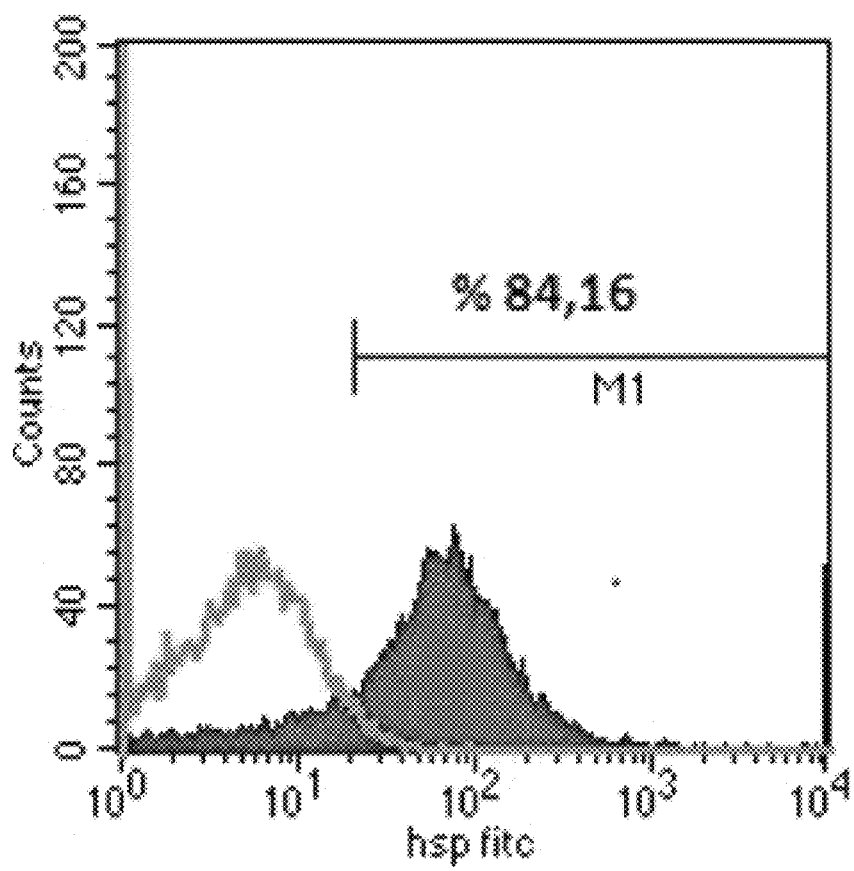
FIG. 8 is a view of the flow cytometry wherein presence of the plant exosome obtained from wheat plant is determined by HSP 70 surface marker.

By means of the developed isolation method, exosome was obtained preferably by using wheatgrass. This product was subjected to characterization experiments and activity of the cancer and wound healing properties thereof are proved by the results. In the data obtained in the electron microscope image, it was found that the vesicles that were viewed showed similarities with the electron microscope images of exosome in the literature (FIG. 7). The results in the flow cytometry have shown that exosomes express surface marker by 84.16%. This is one of the evidences proving that the molecule we have obtained is exosome (FIG. 8).

It was proven by the MTS result that exposure of the healthy cells to plant exosome serum causes proliferation in the cells. The amount of absorbance which has increased compared to the negative control has shown that viability has increased. The analyses made accordingly proved that wheat exosome increased cell division rate in healthy cells (FIGS. 3A-3F).

24 hours after the 22RV1 cells were treated with serum at concentrations of 5 µg/ml, 10 µg/ml, 15 µg/ml; Annexin V method was applied by using flow cytometry in order to observe cell death. In line with these results, when necrosis and apoptosis ratios were calculated, cell death ratios of 26.02%, 40.08% and 34.36% were observed at the above mentioned concentrations, respectively (FIGS. 3A-3F).

24 hours after the PNT1A cells were treated with serum at concentrations of 5 µg/ml, 10 µg/ml, 15 µg/ml; Annexin V method was applied by using flow cytometry in order to observe cell death. In line with these results, when necrosis and apoptosis ratios were calculated, cell death ratios of 1.81%, 3.26% and 3.22% were observed, respectively (FIGS. 4A-4F).

24 hours after the MCF-7 cells were treated with serum at concentrations of 5 µg/ml, 10 µg/ml, 15 µg/ml; Annexin V method was applied by using flow cytometry in order to observe cell death. In line with these results, when necrosis and apoptosis ratios were calculated, cell death ratios of 24.96%, 31.13% and 23.49% were observed, respectively (FIGS. 5A-5F).

24 hours after the MCF-10A cells were treated with serum at concentrations of 5 µg/ml, 10 µg/ml, 15 µg/ml; Annexin V method was applied by using flow cytometry in order to observe cell death. In line with these results, when necrosis and apoptosis ratios were examined, cell death ratios of 1.57%, 1.25% and 2.74% were observed, respectively (FIGS. 6A-6F). 24 hours after the A498 cells were treated with serum at concentrations of 5 µg/ml, 10 µg/ml, 15 µg/ml; Annexin V method was applied by using flow cytometry in order to observe cell death. In line with these results, when necrosis and apoptosis ratios were calculated, cell death ratios of 51.05%, 38.01% and 42.76% were observed, respectively (FIGS. 1A-1F).

24 hours after the HEK 293 cells were treated with serum at concentrations of 5 µg/ml, 10 µg/ml, 15 µg/ml; Annexin V method was applied by using flow cytometry in order to observe cell death. In line with these results, when necrosis and apoptosis ratios were examined, cell death ratios of 1.79%, 1.63% and 3.16% were observed, respectively (FIGS. 2A-2F).

As a result of the experimental studies, it was proved that the product of the present invention triggers cellular suicide mechanism in the body causing death of cancer cells. It was observed that the treatment applied with the present product has eliminated the disadvantage of damaging the healthy cells while killing the cancer cells which is frequently encountered in chemotherapy treatments.

As a result of the wound model formed based on the MTS result, it was proved that the wound model in the cells treated with the product of the present invention showed much faster healing in comparison to the untreated control cells. This has shown that the obtained product, particularly the product derived from wheat exosome, positively affects and accelerates the process in wound healing and tissue repairing models.

Application of the Invention

The present invention is mainly applied in prostate cancer, breast cancer, kidney cancer; while being also active in pancreas, liver, bone, skin, brain, lung, pleura, uterus, ovary, stomach, intestine, bladder, blood, lymph, thyroid cancer types.

The product of the present invention can be produced in serum form in liquid state primarily while it can also be produced in a solid or hydrogel form. These can be in the form of serum, syrup, tablet, drug, gel and cream. Additionally, another active substance (such as a drug, chemical) can be carried into the cell by using a nano-carrier molecule. This carrying method can be used in various forms and formulations as stated above.

What is claimed is:

1. A product for cancer treatment, comprising a plant derived exosome, wherein a source of the plant derived exosome is wheatgrass or garlic or comprises a combination of wheatgrass, ginger and garlic.

2. The product according to claim 1, wherein, the product is wound healing.

3. The product according to claim 1, wherein, the product is in a form of serum, syrup, tablet, drug, gel or cream.

4. The product according to claim 1, wherein, the product is active against prostate, breast, kidney, pancreas, liver, bone, skin, brain, lung, pleura, uterus, ovary, stomach, intestine, bladder, blood, lymph, and thyroid cancer.

5. The product according to claim 2, wherein, the product is in a form of serum, syrup, tablet, drug, gel or cream.

6. The product according to claim 2, wherein, the product is active against prostate, breast, kidney, pancreas, liver, bone, skin, brain, lung, pleura, uterus, ovary, stomach, intestine, bladder, blood, lymph, and thyroid cancer.

7. The product according to claim 3, wherein, the product is active against prostate, breast, kidney, pancreas, liver, bone, skin, brain, lung, pleura, uterus, ovary, stomach, intestine, bladder, blood, lymph, and thyroid cancer.

* * * * *